United States Patent [19]

Paterson

[11] Patent Number: 5,599,344
[45] Date of Patent: Feb. 4, 1997

[54] CONTROL APPARATUS FOR ELECTROSURGICAL GENERATOR POWER OUTPUT

[75] Inventor: William G. Paterson, Longmont, Colo.

[73] Assignee: Valleylab Inc., Boulder, Colo.

[21] Appl. No.: 468,950

[22] Filed: Jun. 6, 1995

[51] Int. Cl.⁶ .................................................. A61H 5/00
[52] U.S. Cl. ................................................ 606/34; 606/32
[58] Field of Search ............................................ 606/32–52

[56] References Cited

U.S. PATENT DOCUMENTS

| | | | |
|---|---|---|---|
| 4,658,819 | 4/1987 | Harris et al. | |
| 4,961,047 | 10/1990 | Carder | 606/35 |
| 5,370,645 | 12/1994 | Klicek et al. | 606/35 |
| 5,403,312 | 4/1995 | Yates et al. | 606/46 |

*Primary Examiner*—David M. Shay
*Attorney, Agent, or Firm*—Peter C. Richardson; Lawrence C. Akers; Aaron Passman

[57] ABSTRACT

A power control apparatus for an electrosurgical generator is used for controlling output power from the generator to the tissue or bodily fluids of a patient. The control apparatus rapidly determines the range of impedance of the load on the electrosurgical generator and adjusts the output power accordingly. Output current and output voltage from the electrosurgical generator are monitored and sent to a microprocessor. The microprocessor runs an algorithm that determines the impedance range of the load on the generator. The algorithm uses computational techniques, such as comparisons and bit shifting, that avoid long division and other time-consuming operations. The microprocessor can then adjust a high voltage power supply that effects the radio frequency amplifier stage. A method for controlling the power of the electrosurgical generator, including steps in the algorithm, is also disclosed.

8 Claims, 2 Drawing Sheets

CONTROL APPARATUS FOR ELECTROSURGICAL GENERATOR POWER OUTPUT

Related applications incorporated herein and made a part hereof by reference and filed on the same date as this application:

Power Control for An Electrosurgical Generator; U.S. Ser. No. 08/471,116;

Digital Waveform Generation for Electrosurgical Generators; U.S. Ser. No. 08/471,344;

A Control System for Neurosurgery; U.S. Ser. No. 08/470,533; PC9162;

Exit Spark Control for an Electrosurgical Generator; U.S. Ser. No. 08/479,424; PC9217.

FIELD OF THE INVENTION

Invention This invention relates to an apparatus and method for controlling power from an electrosurgical generator based on the impedance range of the tissue being treated, and more particularly to an apparatus and method for more rapidly estimating the impedance range of the tissue being treated by an electrosurgical generator by bit shifting in the binary system and comparison, instead of mathematically dividing the voltage by the current to determine impedance and then using that to select the electrosurgical treatment for the tissue.

BACKGROUND OF THE DISCLOSURE

Electrosurgical generators are used for surgically treating the tissue and bodily fluids of a patient. One of the important features of an electrosurgical generator is the ability to control the output power. Surgeons prefer to work with electrosurgical generators that can deliver a controlled level of power to the tissue. This is because a controlled power level is safer and more effective in surgery.

One of the factors that effects the output power is the electrical load on the generator that is presented by the tissue and bodily fluids of the patient. In particular, the impedance of the tissue that is being treated will change as electrosurgical energy is applied. It is therefore desirable for electrosurgical generators to monitor the impedance of the load and adjust promptly the output power accordingly and effectively. As different types of tissue and bodily fluids are encountered the impedance changes and the response time of the electrosurgical control of output power must be rapid enough to seemlessly permit the surgeon to treat the tissue. Moreover the same tissue type can be desiccated during electrosurgical treatment and thus its impedance will change dramatically in the space of a very brief time. The electrosurgical output power control has to respond to that impedance change as well.

Designers of electrosurgical generators define the behavior of the output power according to power curves. These curves describe the RMS power delivered to the patient as a function of impedance of the load. It is possible to divide the power curve into regions based on the impedance level of the load as measured. At low impedance levels, the electrosurgical generator may be designed to limit the current flowing to the patient. At high impedance levels, the electrosurgical generator may by design be voltage limited. In other ranges of impedance, the electrosurgical generator may be designed to maintain a constant level of RMS power supplied to the patient.

A control apparatus for an electrosurgical generator may be required to change its method of power regulation based on the region of impedance. For example, the generator may change from a current limiting mode, to a constant power mode, and then to a voltage limiting mode. Rapid computational methods are required to affect this kind of mode switching and response to varying tissue impedance during electrosurgery.

SUMMARY OF THE INVENTION

This invention describes a microprocessor based control system for an electrosurgical generator that can rapidly switch modes of operation. The control system monitors the output voltage and output current at the patient circuit to in effect find the instantaneous impedance changes. The microprocessor executes an algorithm that rapidly determines the approximate range of load impedance based on the monitored current and voltage signals. The control system is then able to properly select a mode of operation and control the output power accordingly.

The rapid determination of impedance range is accomplished by the microprocessor algorithm. That algorithm is designed to avoid complex and slow mathematical manipulations by taking advantage of simplifying assumptions that minimize mathematical manipulations.

It has been found that an exact calculation of impedance is not required for effective operation of the control system. That is, only the general range of impedance is required to successfully operate. Surprisingly, the general range of impedance can be obtained by the algorithm without instantaneously calculating the impedance, but by taking advantage of rapid bit shifting in a microprocessor.

Microprocessors can perform a bit shift more rapidly than executing other mathematical operations. A bit shift may be either to the right or to the left. A bit shift is simply the process of shifting each bit in a binary stream in the same direction. A bit shift to the right can be mathematically described as or is the equivalent to dividing by two. Conversely, a bit shift to the left can be mathematically identical to or described as multiplying by two. The speed of the microprocessor in handling all and not just some of the bit shifting operations is productively applied in the apparatus and method of this system.

Ranges of impedance may be defined for purposes of controlling the output of the electrosurgical generator; that is to say that the electrosurgical generator power output is preferably controlled in accord with the impedance in a given range. Tissue types are thus broadly categorized according to the impedance range into which each may be placed for purposes of output power level. In using the binary system, it is important that the breakpoints that define the ranges are related by factors of two. For example, a low range of impedance may be from 0 to 16 ohms, a mid range of impedance may be from 16 to 512 ohms, and a high range of impedance may be impedances above 512 ohms in a preferred electrosurgical generator control system. U.S. Pat. No. 4,658,819 discloses a power curve for control of the application of electrosurgical power to a bipolar instrument. Significant to the '819 teaching is the initial constant current application of energy, then the constant power application of energy and finally the decrease of the power output in accord with the square of the impedance. Notable is the lack of any appreciation of the control of the application of energy as a function of identified impedance values after applying a source of constant current, then after applying a source of constant power and finally after applying a factored source of constant voltage.

The control system for the generator only needs to identify the range of the impedance of the generator load, i.e. tissue and bodily fluids. As expressed, the time needed for an exact calculation of impedance is not required. As the tissue of a patient is electrosurgically treated, it is often the situation that, the range of impedance may move from a low level to a middle amount, and then from the middle amount to a high level. It is functionally efficient to the operation of the control system that transitions from one range to the next be quickly recognized.

A voltage sensor and a current sensor are used to monitor the electrosurgical generator output voltage and output current, respectively during an operative procedure. Each of those aforesaid sensor outputs are expressed as a varying (with time) voltage that is proportional to the particular monitored signal. The outputs from the sensors are converted to a digital format and read by the microprocessor. These values may be referred to as the scaled voltage and the scaled current, respectively because a scaling factor is for convenience used to prepare each. The scaling of the voltage and current signals are performed so that they are equal in magnitude when they represent an impedance breakpoint.

The algorithm in the microprocessor may preferably determine the range of the load impedance. The impedance of the load may be described by the ratio of the scaled voltage to the scaled current. However, computing those particular values of those ratios would take too much time in the microprocessor. Instead of computing each ratio for the changing voltage and current, the algorithm uses a bit shifting technique to examine the voltage and current with respect to one another to find the range of impedance within specified breakpoints.

In particular, multiplying factors are preferably applied to the digitized voltage and current signals by the algorithm to arbitrarily set the scaled voltage and the scaled current equal to one another for the condition where the impedance is at a convenient breakpoint. Once the multiplying factors have been applied, the impedance range can be assessed by a combination of comparisons and bit shifting. For example, initially the scaled voltage is compared with the scaled current. If the scaled voltage is smaller than the scaled current, the scaled voltage may be bit shifted to the left which corresponds to multiplication by two. Next, the scaled voltage and the scaled current are compared again. If the scaled voltage is now larger than the scaled current, then the impedance range can be inferred as follows: the impedance when the scaled voltage is equal to the scaled current is known (because it was set by the scale factors); since the scaled voltage is smaller than the scaled current, then the impedance must be lower than the known set impedance; since only one bit shift was required to make the scaled voltage greater than the scaled current, it can be inferred that the impedance was originally within a factor of two lower than the known set impedance. If, after the first bit shift, the scaled voltage is still smaller than the scaled current, the process of bit shifting and comparing must be repeated. Of course where the bit shifting starts and which way, left or right, it is performed is purely arbitrary. The choice is logically a consequence of what experience would lead the designer to believe will be found to be the impedance. Therefore the selection of where to start and which way to proceed is based on experience with an appreciation of the need for speed and efficiency.

A numerical example is provided for purposes of illustration. Suppose that multiplying factors are chosen such that the scaled voltage is equal to the scaled current when the impedance is at 32 ohms. Assume also that there are three impedance ranges of interest: a first range from 0 to 8 ohms, and a second range from 8 to 32 ohms, and a third range from 32 to 128 ohms. Suppose that the instantaneous value of the scaled voltage is 00001000 as a binary number, which is 8 decimal. Suppose that the instantaneous value of the scaled current is 00001100 as a binary number, which is 12 decimal. The algorithm compares the two scaled values and determines that scaled voltage is less than scaled current (8 >12). Therefore, the impedance has been found to be less than 32 ohms and most importantly not in the third range.

However, the algorithm must further determine whether the impedance is in the first range or the second range. Therefore, the algorithm will bit shift the scaled voltage to obtain 00010000, a binary number, which is 16 decimal. Next, the algorithm repeats the comparison of scaled voltage to scaled current and finds that the scaled voltage is now more than the scaled current (16>12). Therefore, the impedance has been found in the second range. That is the information needed to control the output power of the electrosurgical generator because the generator is controlled to only the range of impedance.

There are several ways of executing the same basic algorithm. For example, the scaled current could be bit shifted instead of the scaled voltage. Also, there may be any number of breakpoints, as long as the breakpoints are related by powers of two.

Once the range of impedance has been determined, the microprocessor can specifically in the preferred execution issue appropriate commands to an adjustable high voltage power supply. For example, if the impedance is found in a range where constant power is desired, the microprocessor will issue commands to maintain the power constant.

DETAILED DESCRIPTION OF THE INVENTION

Figure 1:
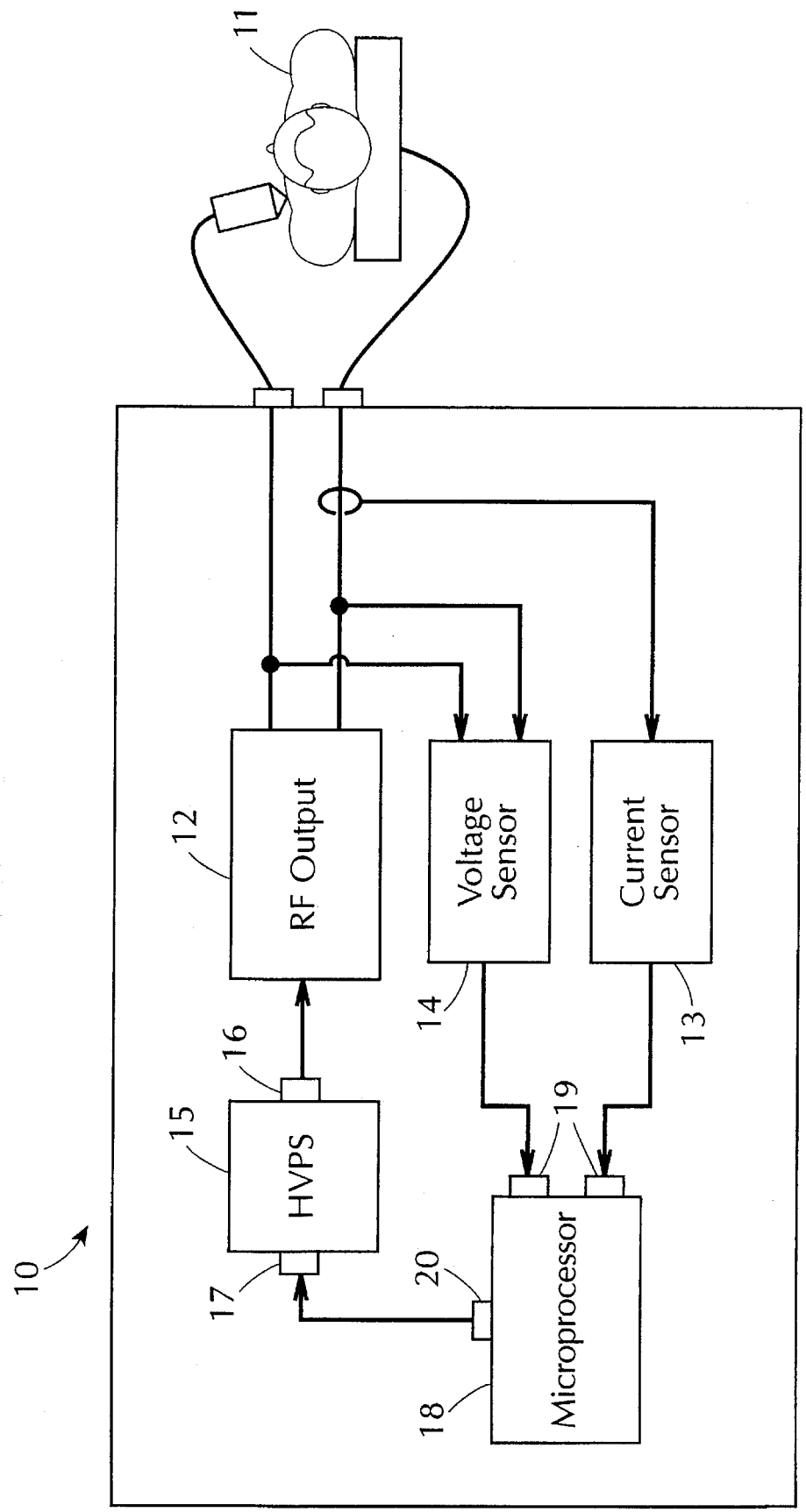
FIG. 1 is a schematic block diagram of an electrosurgical system.
Figure 2:
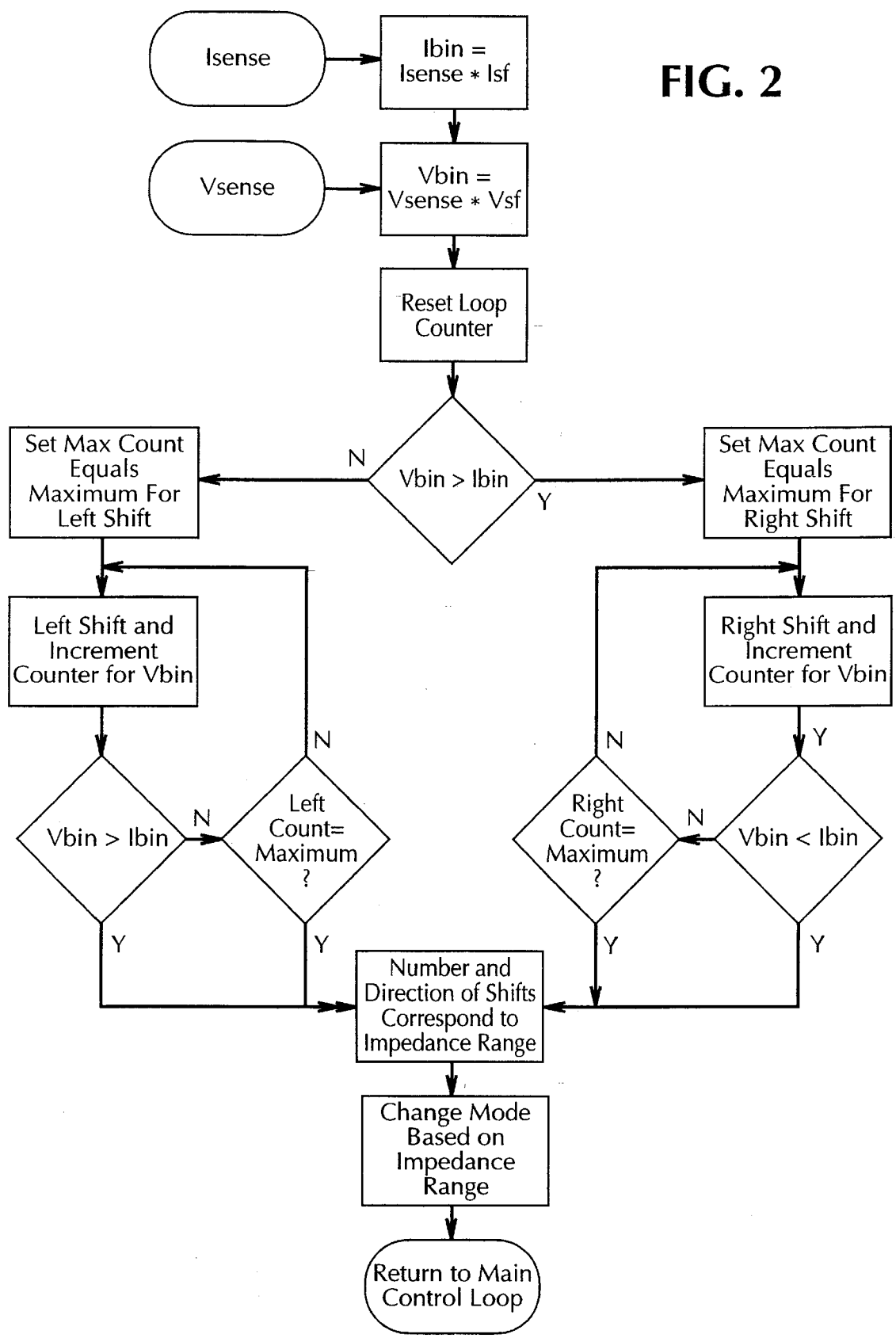
FIG. 2 is a flow diagram showing the main steps followed for controlling power based on the impedance range by rapidly estimating the impedance using bit shifting in the binary system.

A power control apparatus for an electrosurgical generator is used for controlling output power from the generator to the tissue or bodily fluids of a patient. A radio frequency output stage in the electrosurgical generator is used for generating an output current and an output voltage. A current sensor in the electrosurgical generator is electrically connected to produce a current signal proportional to the output current, and a voltage sensor in the electrosurgical generator is electrically connected to produce a voltage signal proportional to the output voltage.

An adjustable high voltage power supply has an output connected to the radio frequency output stage. The power supply preferably has an adjuster for adjusting the high voltage power supply. The control system adjusts the high voltage power supply differently depending on the range of impedance of the load on the electrosurgical generator.

A microprocessor in the electrosurgical generator has a plurality of input ports and at least one output port. A first input port is preferably in electrical connection with the voltage signal, a second input port is preferably in electrical connection with the current signal. An output port is in electrical connection with the adjustor for the high voltage power supply.

A algorithm is most preferably stored in the microprocessor. The algorithm is used for generating signals for the first output port of the microprocessor. The algorithm represents the voltage signal as a first scaled binary number and represents the current signal as a second scaled binary number. The algorithm next compares the first scaled binary number with the second scaled binary number, and if an inequality is found the algorithm will bit shift either of the scaled binary numbers until the relative magnitude of the first scaled binary number changes with respect the second scaled binary number, The algorithm next will generate signals for the first output port of the microprocessor based on the bit shifts that were required to change the relative magnitudes. The purpose of the bit shifting is to determine the range of impedance of the load on the electrosurgical generator.

Bit shifting is an alternative to long division in the calculation of impedance. In the preferred embodiment, the microprocessor is a Phillips 80C562 microcontroller with an 11.059 megahertz clock and using a Franklin C51 8051 compiler then an algorithm that uses long division to compute impedance requires 1445 microseconds, whereas the bit shifting algorithm requires only 85 microseconds.

The first output port of the microprocessor is most preferably electrically manipulating the adjustor for the high voltage power supply to deliver a desired output power from the radio frequency output stage.

A method for controlling the output power of an electrosurgical generator is also disclosed. The method comprises the steps of: generating an output current and an output voltage with a radio frequency output stage in the electrosurgical generator; producing a current signal proportional to the output current with a current sensor in the electrosurgical generator; representing the current signal as a first scaled binary number in a microprocessor; producing a voltage signal proportional to the output voltage with a voltage sensor in the electrosurgical generator; representing the voltage signal as a second scaled binary number in a microprocessor; comparing the first scaled binary number with the second scaled binary number; bit shifting either of the scaled binary numbers until the first scaled binary number changes in magnitude with respect to the second scaled binary number; estimating a range of impedance of the tissue or bodily fluids of the patient based on the bit shifts that were executed; adjusting a high voltage power supply based on the estimated range of impedance; and amplifying the radio frequency output stage in the electrosurgical generator with the adjustable high voltage power supply.

In the preferred embodiment, the method will further comprise the steps of defining a first range of impedance wherein the output power will be held constant whenever the estimated impedance is within the first range; defining a second range of impedance wherein the output current will be held constant whenever the estimated impedance is within the second range; and defining a third range of impedance wherein the output voltage will be held constant whenever the estimated impedance is within the third range.

While a particular approach to finding the impedance range has been disclosed and a specific electrosurgical output power control system has by way of example been explained, it will be understood that many variations of this invention are possible. Various details of the design and the algorithm may be modified without departing from the true spirit and scope of the invention as set forth in the appended claims.

What is claimed is:

1. A power control apparatus for an electrosurgical generator for use in controlling output power from the generator to the tissue or bodily fluids of a patient, the power control apparatus comprising:

a radio frequency output stage in the electrosurgical generator for generating an output current and an output voltage;

a current sensor in the electrosurgical generator which is electrically connected to receive the output current and to produce a current signal proportional to the output current;

a voltage sensor in the electrosurgical generator which is electrically connected to receive the output voltage and to produce a voltage signal proportional to the output voltage;

a microprocessor in the electrosurgical generator having a plurality of input ports and at least one output port, wherein a first input port is electrical connection with the voltage signal, a second input port is in electrical connection with the current signal;

an algorithm in the microprocessor for generating signals for the at least one output port of the microprocessor, the algorithm first expressing the voltage signal as a first scaled binary number and expressing the current signal as a second scaled binary number, the algorithm next comparing the first scaled binary number with the second scaled binary number, and if an inequality is found between the first binary number and the second binary number the algorithm will bit shift the first or the second scaled binary number to determine a range of impedance, the algorithm programmed to then generate signals for the output port of the microprocessor based on the range of impedance, and the microprocessor thereby controlling the output power.

2. The power control apparatus for an electrosurgical generator of claim 1 further comprising an adjustable high voltage power supply having an output connected to the radio frequency output stage, and having an adjustor for adjusting voltage of the high voltage power supply, wherein the at least one output port includes a first output port which is in electrical connection with the adjustor for the high voltage power supply, and wherein the first output port electrically manipulates the adjustor for the high voltage power supply to deliver output power.

3. A method for controlling output power of an electrosurgical generator which is being used on the tissue or bodily fluids of a patient, the method comprising the steps of:

generating an output current and an output voltage with a radio frequency output stage in the electrosurgical generator;

producing a current signal proportional to the output current with a current sensor in the electrosurgical generator;

representing the current signal as a first scaled binary number in a microprocessor;

producing a voltage signal proportional to the output voltage with a voltage sensor in the electrosurgical generator;

representing the voltage signal as a second scaled binary number in a microprocessor;

comparing the first scaled binary number with the second scaled binary number;

bit shifting either of the scaled binary numbers until the first scaled binary number minus the second scaled binary number changes in sign, and ascertaining a range of impedance of the tissue or bodily fluids of the patient based on the bit shifts that were executed and controlling the output power by adjusting the output voltage according to the range of impedance.

4. The method of claim 3 further comprising the step of adjusting a high voltage power supply based on the estimated range of impedance.

5. The method of claim 4 further comprising the step of amplifying the radio frequency output stage in the electrosurgical generator with the adjustable high voltage power supply.

6. The method of claim 5 further comprising the step of defining a first range of impedance wherein the output power will be held constant whenever the estimated impedance is within the first range.

7. The method of claim 5 further comprising the step of defining a second range of impedance wherein the output current will be held constant whenever the estimated impedance is within the second range.

8. The method of claim 5 further comprising the step of defining a third range of impedance wherein the output voltage will be held constant whenever the estimated impedance is within the third range.

\* \* \* \* \*